United States Patent [19]

Komai et al.

[11] Patent Number: 4,469,862
[45] Date of Patent: Sep. 4, 1984

[54] POLYMERIC DIACYL PEROXIDES

[75] Inventors: Takeshi Komai; Toshihiro Izumi; Syuji Suyama, all of Chita, Japan

[73] Assignee: Nippon Oil and Fats Co. Ltd., Japan

[21] Appl. No.: 508,197

[22] Filed: Jun. 27, 1983

[30] Foreign Application Priority Data

Jul. 5, 1982 [JP] Japan ................................ 57-116619
Aug. 26, 1982 [JP] Japan ................................ 57-146807
Nov. 18, 1982 [JP] Japan ................................ 57-202725
Mar. 28, 1983 [JP] Japan ................................ 58-52139

[51] Int. Cl.$^3$ ............................................. C08G 67/00
[52] U.S. Cl. .................................... 528/271; 568/561; 526/232; 526/232.3
[58] Field of Search ......................... 528/271; 568/561

[56] References Cited

U.S. PATENT DOCUMENTS 3,671,651 6/1972 D'Angelo .............................. 528/271
4,283,512 8/1981 Matsushima .......................... 528/271

Primary Examiner—Paul R. Michl
Attorney, Agent, or Firm—Parkhurst & Oliff

[57] ABSTRACT

An industrially highly valuable novel polymeric diacyl peroxide which is used as a polymerization initiator for free radical polymerization of vinyl monomer, and which is appreciably safe in production and handling, rapidly soluble in vinyl monomer with high solubility, and has exceedingly high catalyst efficiency in the free radical polymerization of vinyl monomer.

7 Claims, No Drawings

POLYMERIC DIACYL PEROXIDES

BACKGROUND OF THE INVENTION

1. Field of the Invention

The present invention relates to a novel polymeric diacyl peroxide having a branched hydrocarbon group in the molecule, which is used as an initiator for free radical polymerization of vinyl monomer.

2. Description of the Prior Art

Heretofore, polymeric diacyl peroxides have been publicly known which are obtained by polycondensation of dicarboxylic acid chlorides and sodium peroxide. That is, Berichte, vol. 27, p. 1510 (1894) reports a polymeric diacyl peroxide obtained by polycondensation of phthalic chloride and sodium peroxide, J. Amer. Chem. Soc., vol. 68, p. 534 (1946) reports polymeric diacyl peroxide obtained by reacting oxalic chloride with sodium peroxide, and Chem. Abst, vol. 60, 5293d and 10892e (1964) reports a polymeric diacyl peroxide having the following formula:

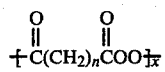

wherein n is 2–10 and x is 16–35 obtained by reacting aliphatic dicarboxylic acid chloride with sodium peroxide. Further, Japanese patent application laid-open No. 149,918/78 discloses a polymeric diacyl peroxide having an ester bond in the molecule obtained by reacting an acid chloride having an ester bond in the molecule with sodium peroxide.

It has been publicly known also that the above described polymeric diacyl peroxides are useful as initiators for free radical polymerization (hereinafter abbreviated as "polymerization initiator") of vinyl monomer. For example, Chem. Abst, vol. 67, 54445a (1967) reports that if the above polymeric peroxide is used as a polymerization initiator a polymer is obtained having a larger molecular weight which is about twice as much than that obtained by using benzoyl peroxide. Chem. Abst, vol. 84, 136120f (1976) reports that if the above polymeric peroxide is used as a polymerization initiator of vinyl acetate a polymer is obtained having a larger molecular weight and less branching as compared with a polymer obtained by using benzoyl peroxide. Journal of the Chemical Society of Japan vol. 69, p. 718 (1966) reports that if poly(phthaloyl peroxide) is used as a polymerization initiator a styrene-methylmethacrylate graft polymer is obtained.

As mentioned above, the publicly known polymeric diacyl peroxides are useful polymerization initiators. However, the publicly known polymeric diacyl peroxides not having an ester bond in the molecule have drawbacks that; (1) they are detonative compounds sensitive to impact and friction (refer to Chem. Abst, vol. 59, 7651 (1963)), and (2) they have low solubility in organic solvents and are completely or substantially insoluble in vinyl monomer, so that they can not be used as polymerization initiators industrially (refer to Journal of the Chemical Society of Japan vol. 69, p. 718 (1966) and Chem. Abst, vol. 64, 15989g (1968)). This feature has a close relation with catalyst efficiency. If a polymerization initiator of a low solubility is used for polymerization, catalyst efficiency thereof becomes low.

The aforementioned polymeric diacyl peroxide having an ester bond in the molecule has an advantage of improving the above described two drawbacks, however, it has the following shortcomings. Namely, the material acid chloride having an ester bond in the molecule is produced by a two-steps process under a dry air or nitrogen stream, so that its production requires a prolonged time and special devices and hence it is time consuming and expensive in cost and commercially disadvantageous.

SUMMARY OF THE INVENTION

The inventors have made many studies and experiments to eliminate the above mentioned drawbacks and shortcomings which have been encountered with the prior art techniques.

An object of the present invention is to provide a novel polymeric diacyl peroxide which is highly useful industrially as a polymerization initiator for vinyl monomer.

Another object of the present invention is to provide a novel polymeric diacyl peroxide which is safe in production and handling.

A further object of the present invention is to provide a novel polymeric diacyl peroxide which dissolves rapidly in vinyl monomer with high solubility.

A still further object of the present invention is to provide a novel polymeric diacyl peroxide which has a high catalyst efficiency.

A feature of the present invention is the provision of a novel polymeric diacyl peroxide which consists essentially of a randomly oriented repeated structural unit of a general formula:

wherein X represents a group selected from the group consisting of

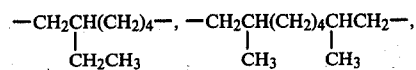

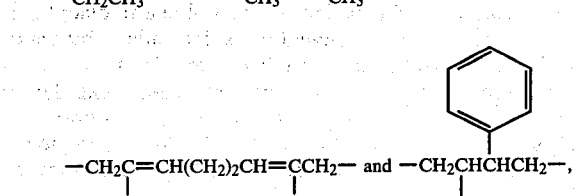
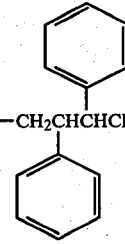

and which has a mean molecular weight of 1,400–18,000.

Further objects and features of the present invention will be fully understood from the following detailed description.

Polymeric diacyl peroxide of the present invention can be produced by the following method.

Namely, 7-ethylhexadecane-1,16-dicarboxylic acid chloride, 7,12-dimethyloctadecane-1,20-dicarboxylic acid chloride, 7,12-dimethyl-7,11-octadecadiene-1,18-dicarboxylic acid chloride or 7,8-diphenyltetradecane-1,14-dicarboxylic acid chloride is added little by little to an aqueous solution of a peroxidized reagent such as sodium peroxide, potassium peroxide or the like, and reacted, while agitating. After completion of the reaction, the reaction product is separated from the waste reaction liquor to easily obtain the desired polymeric diacyl peroxide.

Reaction condition is the same as in the case of producing a usual diacyl peroxide. That is, reaction temperature is $-10°$ C.$-+40°$ C., preferably $0°-15°$ C., and reaction time is 0.25-5 hrs., preferably 0.5-2 hrs.

Mol ratio of the material dicarboxylic acid chloride to the peroxidized reagent is 1:0.7-3, and concentration of aqueous solution of peroxidized reagent is 1-15 wt%, preferably 2-10 wt%.

Thus produced polymeric diacyl peroxide of the present invention is a transparent viscous liquid consisting essentially of the above structural unit (1), and is a random concentration polymer wherein the structural units are oriented or bonded mutually as a head to head bond, head to tail bond or tail to tail bond, having a mean molecular weight of 1,400-18,000.

The polymeric diacyl peroxide of the present invention is confirmed to have C—O bond and

bond of diacyl and —O—O— bond of peroxide by IRA spectrum, and is identified by NMR spectrum to have the structures of

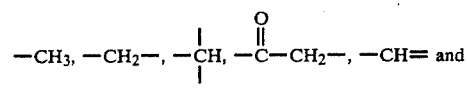

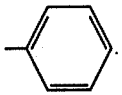

Thus, the structural unit of the polymeric diacyl peroxide is determined.

Mean molecular weight of the polymeric diacyl peroxide of the present invention is determined by vapor pressure osmometric method (abridged as VPO method) using a molecular weight determining device type 117 made by Corona Denki K.K. In addition, active oxygen content of the polymeric diacyl peroxide of the present invention is determined by iodine titration method.

The polymeric diacyl peroxide according to the present invention has many advantages as follows.

(1) It is insensitive to impact and friction and less explosive and safe in production and handling.

(2) It has a widely improved solubility in organic solvents as compared with conventional polymeric diacyl peroxide. For example, it dissolves well in aromatic hydrocarbons such as benzene, toluene and the like, esters such as ethylacetate, butylacetate and the like, cyclic ethers such as dioxane, tetrahydrofuran and the like, ketones such as methylethylketone and the like, chloroform, carbon tetrachloride and the like. Therefore, it dissolves rapidly in a vinyl monomer when added to the vinyl monomer as a polymerization initiator, so that workability in case of industrial utilization is largely improved.

(3) It has high catalyst efficiency at the time of initiating the polymerization. That is, its catayst efficiency is about twice as much as that obtained by using a conventional polymeric peroxide.

(4) The polymeric diacyl peroxide of the present invention has many peroxide groups in the molecule, so that it can perform particular polymerization reactions that can never be achieved by using usual peroxides. For example, if the polymeric diacyl peroxide of the present invention is used for polymerizing styrene monomer, polystyrene is obtained having a molecular weight about twice as much than that obtained by using benzoyl peroxide or lauroyl peroxide.

Illustrative vinyl monomers that can be polymerized by the polymeric diacyl peroxide of the present invention are, for example, vinyl acetate, acrylate ester, methacrylate ester, acrylonitrile, vinylidene chloride, vinyl chloride, ethylene and the like, in addition to styrene.

(5) The polymeric diacyl peroxide of the present invention can be used for polymerization of two types of vinyl monomers to produce a so-called "block copolymer". For instance, in the first step, styrene is polymerized by this polymeric diacyl peroxide to incorporate at least one peroxide group in the resulting polystyrene, and, in the second step, the resultant polystyrene containing the peroxide group is polymerized with a different type of vinyl monomer such as methylmethacrylate to obtain a block copolymer. Especially, if the polymeric diacyl peroxide of the present invention is used for the purpose of obtaining the block copolymer, production yield or efficiency of the block copolymer is noticeably improved because of its excellent solubility in vinyl monomer as mentioned above.

In the first step of polymerization, if a conventional polymeric diacyl peroxide having a low solubility in vinyl monomer is used as a polymerization initiator, polymerization starts only at surfaces of partially soluble portion or insoluble portion thereof, so that a relatively small amount of peroxide group enters in the polymer chain and a large amount of polymeric diacyl peroxide remains unreacted. So, if the reaction mixture of the first step is used in the second step of polymerization, homopolymer of vinyl monomer is naturally produced as a by-product resulting in decrease of production efficiency of block homopolymer. To avoid such disadvantageous effects, there has been proposed a method wherein the peroxide group-containing polymer is purified by separating the unreacted polymeric diacyl peroxide at the end of the first step of polymerization. However, it is industrially disadvantageous in that the separation operation is difficult to perform and the process is prolonged. Besides, the unreacted polymeric diacyl peroxide remains in vain without being used effectively resulting in loss of a raw material.

Vinyl monomer which can be used for preparing a block copolymer using the polymeric diacyl peroxide of the present invention is, of course, not limited to the aforementioned example and any combination of vinyl monomers can be used so far as they can be polymerized by the polymeric diacyl peroxide of the present invention.

As explained above, the polymeric diacyl peroxide of the present invention is safe in production and handling and rapidly dissolves in vinyl monomer when added thereto as a polymerization initiator and exhibits an excellent catalyst efficiency as a polymerization initiator, so that it is eminently useful industrially.

Hereinafter, the present invention will be explained in more detail with reference to examples.

DESCRIPTION OF THE PREFERRED EMBODIMENTS

EXAMPLE 1

In a four-necked flask equipped with a stirrer and a thermometer, 137 g (0.24 mol) of 7% sodium hydroxide aqueous solution and 8.2 g (0.12 mol) of 50% hydrogen peroxide are mixed to prepare an aqueous solution of sodium peroxide. Subsequently, a solution of 38 g (0.1 mol) of 7-ethyl-hexadecane-1,16-dicarboxylic acid chloride (commercial product having a purity of 99% made by Okamura Seiyu K.K. using a raw material dicarboxylic acid of an acid value of 330) in 40 g of toluene is added thereto little by little at 0°–5° C. while agitating. The agitation is continued at this temperature for 30 minutes and thereafter the mixture is neutralized to pH 7 by adding dilute hydrochloric acid thereto. Then, the oily phase is taken out, washed twice with water, dried over anhydrous magnesium sulfate, filtrated to remove solid substances and distilled under reduced pressure to remove the solvent toluene and to obtain 29 g of a transparent viscous liquid.

The viscous liquid has an active oxygen content of 4.28% determinable by a usual iodine titration method Characteristic absorption wave lengths of the viscous liquid in IRA spectrum are $1,780$ cm$^{-1}$, $1,800$ cm$^{-1}$ $$(C=O$$

bond of diacyl group), $1050$ cm$^{-1}$ (C—O bond) and $880$ cm$^{-1}$ (—O—O—bond).

$\delta$ values and strengths of NMR spectrum of the viscous liquid are

| | | |
|---|---|---|
| ⓐ | 0.82 ppm | (3H) |
| ⓑ | 1.28 ppm | (24H) |
| ⓒ | 1.72 ppm | (5H) |
| ⓓ | 2.36 ppm | (4H) |

From the above data, it is confirmed that the viscous liquid is a polymeric diacyl peroxide essentially consisting of a structural unit having a formula:

$$\begin{array}{c} ⓓ \;\; ⓒ \;\; ⓑ \;\; ⓒⓑ \;\; ⓒ \;\; ⓓ \\ \phantom{x}\overset{O}{\underset{\|}{C}}CH_2CH_2(CH_2)_4\underset{\underset{\underset{ⓑ \phantom{x} ⓐ}{CH_2-CH_3}}{|}}{\overset{H}{C}}(CH_2)_7CH_2CH_2\overset{O}{\underset{\|}{C}}OO \end{array}$$

The polymeric diacyl peroxide has a mean molecular weight of 9,280 (n≈27.3, wherein n denotes a number of repeating the structural unit) by usual VPO method.

The safety degree of the polymeric diacyl peroxide is determined by the method described in Safety Engineering, vol. 4, number 2, p. 181 (1965). The results are shown in Table 1 which will later be described.

Solubility of the polymeric diacyl peroxide is determined by measuring an amount thereof which dissolves in various solvents (100 g) at 25° C. The results are shown in Table 2 which will also later be described.

EXAMPLE 2

The same reaction, with separation and purification as in Example 1 is repeated, except that the amount of hydrogen peroxide is 5.5 g (0.08 mol) instead of 8.2 g (0.12 mol) and 38 g (0.12 mol) of dichloride of 7-ethyl-hexadecane-1,16-dicarboxylic acid having an acid value of 307 of Okamura Seiyu K.K. (trade name OSK-DA SB-20) is used, to obtain 26 g of a transparent viscous liquid.

The viscous liquid has an active oxygen content of 3.69% measured by the usual iodine titration method as in Example 1.

The viscous liquid has the same characteristic absorption waves in IRA spectrum and the same $\delta$ and strength values in NMR spectrum as those of the product of Example 1, so that it is confirmed that it consists of the same structural unit with the polymeric diacyl peroxide of Example 1.

The polymeric diacyl peroxide has a mean molecular weight of 2,200 (n≈6.5) determined by a similar manner as in Example 1.

EXAMPLE 3

The same reaction, with separation and purification as in Example 1 is repeated, except that 134.7 g (0.24 mol) of 10% potassium hydroxide aqueous solution is used instead of 137 g (0.24 mol) of 7% sodium hydroxide aqueous solution and the amount of 50% hydrogen peroxide is 6.8 g (0.10 mol) instead of 8.2 g, to obtain 30 g of a transparent viscous liquid.

The viscous liquid has an active oxygen content of 4.42% measured by the usual iodine titration method of Example 1.

The viscous liquid has the same characteristic absorption waves in IRA spectrum and the same $\delta$ and strength values in NMR spectrum as those of the product of Example 1, so that it is confirmed that it consists of the same structural unit with the polymeric diacyl peroxide of Example 1.

The polymeric diacyl peroxide has a mean molecular weight of 15,600 (n≈45.9) determined by a similar manner as in Example 1.

EXAMPLE 4

In a four-necked flask equipped with a stirrer and a thermometer, 137 g (0.24 mol) of 7% sodium hydroxide aqueous solution and 8.2 g (0.12 mol) of 50% hydrogen peroxide are mixed to prepare an aqueous solution of sodium peroxide. Subsequently, a solution of 41 g (0.1 mol) of 7,12-dimethyloctadecane-1,20-dicarboxylic acid chloride (purity 99%) in 40 g of benzene is added thereto little by little at 0°–5° C. while agitating. The agitation is continued at this temperature for 30 minutes and thereafter the mixture is neutralized to pH 7 by adding dilute hydrochloric acid thereto. Then, the oily phase is taken out, washed twice with water, dried over anhydrous magnesium sulfate, filtrated to remove solid substances, and distilled, removing the solvent benzene under reduced pressure to obtain 31 g of a transparent viscous liquid.

The viscous liquid has an active oxygen content of 4.14% measured by the usual iodine titration method of Example 1.

Characteristic absorption wave lengths of the viscous liquid in IRA spectrum are $1,780$ cm$^{-1}$, $1,800$ cm$^{-1}$ $$(\overset{|}{\underset{|}{C}}=O$$

bond of diacyl group), 880 cm$^{-1}$ (—O—O—bond) and 1,050 cm$^{-1}$ (C—O bond).

δ values and strengths of NMR spectrum of the viscous liquid are

| | | |
|---|---|---|
| ⓐ | 0.84 ppm | (6H) |
| ⓑ | 1.28 ppm | (24H) |
| ⓒ | 1.68 ppm | (6H) |
| ⓓ | 2.38 ppm | (4H) |

From the above data, it is confirmed that the viscous liquid is a polymeric diacyl peroxide essentially consisting of a structural unit having a formula:

$$\underset{\underset{ⓐ}{CH_3}}{\overset{ⓓ\ \overset{O}{\underset{\|}{C}}\ ⓑ\ \ \ ⓒ\ ⓑ\ \ \ ⓒ\ ⓑ\ \ \ ⓒ\ ⓓ}{+CCH_2CH_2(CH_2)_4CH(CH_2)_4CH(CH_2)_4CH_2CH_2COO+}}\underset{ⓐ}{\underset{|}{CH_3}}\overset{O}{\underset{\|}{}}$$

The polymeric diacyl peroxide has a mean molecular weight of 9,870 (n≅26.8) determined by a similar manner as in Example 1.

Safety degree of the polymeric diacyl peroxide and solubility thereof in various solvents are determined in a similar manner as in Example 1. The results are respectively shown in Tables 1 and 2 which will later be described.

EXAMPLE 5

The same reaction, with separation and purification as in Example 4 is repeated, except that the amount of the 50% hydrogen peroxide is 5.5 g (0.08 mol) instead of 8.2 g (0.12 mol) and 41 g of dichloride of 7,12-dimethyloctadecane-1,20-dicarboxylic acid having an acid value of 310 made by Okamura Seiyu K.K. (trade name OSK-DA 1PS 22) is used, to obtain 27 g of a transparent viscous liquid.

The viscous liquid has an active oxygen content of 3.42% measured by usual iodine titration method.

The viscous liquid has the same characteristic absorption waves in IRA spectrum and the same δ and strength values in NMR spectrum as those of Example 4, so that it is confirmed that it consists of the same structural unit with the polymeric diacyl peroxide of Example 4.

The polymeric diacyl peroxide has a mean molecular weight of 2,320 (n≅6.3) determined by a similar manner as in Example 1.

EXAMPLE 6

The same reaction, with separation and purification as in Example 4 is repeated, except that 134.7 g (0.24 mol) of 10% potassium hydroxide, aqueous solution is used instead of 137 g (0.24 mol) of 7% sodium hydroxide aqueous solution, to obtain 32 g of a transparent viscous liquid.

The viscous liquid has an active oxygen content of 4.16% measured by usual iodine method as in Example 1.

The viscous liquid has the same characteristic absorption waves in IRA spectrum and the same δ and strength values in NMR spectrum as those of Example 4, so that it is confirmed that it consists of the same structural unit with the polymeric diacyl peroxide of Example 4.

The polymeric diacyl peroxide has a mean molecular weight of 14,700 (n≅39.9) determined by a similar manner as in Example 1.

EXAMPLE 7

In a four-necked flask equipped with a stirrer and a thermometer, 137 g (0.24 mol) of 7% sodium hydroxide aqueous solution and 8.2 g (0.12 mol) of 50% hydrogen peroxide are mixed to prepare an aqueous solution of sodium peroxide. Subsequently, a solution of 40.3 g (0.1 mol) of 7,12-dimethyl-7,11-octadecadiene-1,18-dicarboxylic acid chloride in 40 g of benzene is added thereto little by little at 0°–5° C. while agitating. The agitation is continued at this temperature for 30 minutes and thereafter the mixture is neutralized to pH 7 by adding dilute hydrochloric acid thereto. Then, the oily phase is taken out, washed twice with water, dried over anhydrous magnesium sulfate, filtrated to remove solid substances, and distilled to remove the solvent benzene under reduced pressure to obtain 30.6 g of a transparent, viscous liquid.

The viscous liquid has an active oxygen content of 4.19% measured by usual iodine titration method of Example 1.

Characteristic absorption wave lengths of the viscous liquid in IRA spectrum are 1,780 cm$^{-1}$, 1,800 cm$^{-1}$ $$(\overset{|}{\underset{|}{C}}=O$$

bond of diacyl group), 880 cm$^{-1}$ (—O—O—bond) and 1,060 cm$^{-1}$ (C—O bond).

δ values and strengths of NMR spectrum of the viscous liquid are

| | | |
|---|---|---|
| ⓐ | 1.32 ppm | (12H) |
| ⓑ | 1.48 ppm | (10H) |
| ⓒ | 1.68 ppm | (8H) |
| ⓓ | 2.32 ppm | (4H) |
| ⓔ | 5.10 ppm | (2H) |

From the above data, it is confirmed that the viscous liquid is a polymeric diacyl peroxide essentially consisting of a structural unit having the formula:

$$+\overset{O}{\underset{ⓓ}{\underset{\|}{C}}}\underset{ⓒ}{CH_2}\underset{ⓐ}{CH_2}\underset{ⓒ}{(CH_2)_3}\underset{\underset{ⓑ}{CH_3}}{\underset{|}{CH_2C}}\overset{ⓔ}{=}\underset{ⓑ}{CH(CH_2)_2}\overset{ⓔ}{CH}=\underset{\underset{ⓑ}{CH_3}}{\underset{|}{CCH_2}}\underset{ⓒ}{(CH_2)_3}\underset{ⓐ}{CH_2}\underset{ⓒ}{CH_2}\overset{O}{\underset{ⓓ}{\underset{\|}{C}}}OO+$$

The polymeric diacyl peroxide has a mean molecular weight of 7,600 (n≅20.9) determined by a similar manner as in Example 1.

The safety degree of the polymeric diacyl peroxide and solubility thereof in various solvents are determined in a similar manner as in Example 1. The results are respectively shown in Tables 1 and 2 which will later be described.

EXAMPLE 8

The same reaction, with separation and purification, as in Example 7 is repeated, except that the amount of 50% hydrogen peroxide is 5.5 g (0.08 mol) instead of 8.2 g (0.12 mol), to obtain 26.4 g of a transparent viscous liquid.

The viscous liquid has an active oxygen content of 3.48% measured by usual iodine titration method as in Example 1.

The viscous liquid has the same characteristic absorption waves in IRA spectrum and the same δ and strength values in NMR spectrum as those of Example 7, so that it is confirmed that it consists of the same structural unit with the polymeric diacyl peroxide of Example 7.

The polymeric diacyl peroxide has a mean molecular weight of 1,800 (n≅4.9) determined by a similar manner as in Example 1.

EXAMPLE 9

The same reaction, separation and purification as in Example 7 are repeated, except that 134.7 g (0.24 mol) of 10% potassium hydroxide aqueous solution is used instead of 137 g (0.24 mol) of 7% sodium hydroxide aqueous solution and the amount of hydrogen peroxide is 6.8 g (0.10 mol) instead of 8.2 g (0.12 mol), to obtain 31.9 g of a transparent viscous liquid.

The viscous liquid has an active oxygen content of 4.37% measured by usual iodine titration method as in Example 1.

The viscous liquid has the same characteristic absorption waves in IRA spectrum and the same δ and strength values in NMR spectrum as those of Example 7, so that it is confirmed that it consists of the same structural unit with the polymeric diacyl peroxide of Example 7.

The polymeric diacyl peroxide has a mean molecular weight of 14,200 (n≅39.0) determined by a similar manner as in Example 1.

EXAMPLE 10

In a four-necked flask equipped with a stirrer and a thermometer, 137 g (0.24 mol) of 7% sodium hydroxide aqueous solution and 8.2 g (0.12 mol) of 50% hydrogen peroxide are mixed to prepare an aqueous solution of sodium peroxide. Subsequently, a solution of 47.5 g (0.1 mol) of chloride of 7,8-diphenyltetradecane-1,14-dicarboxylic acid in 45 g of benzene is added thereto little by little at 0°–5° C. while agitating. The agitation is continued at this temperature for 30 minutes and thereafter the mixture is neutralized to pH 7 by adding dilute hydrochloric acid thereto. Then, the oily phase is taken out, washed twice with water, dried over anhydrous magnesium sulfate, filtrated to remove solid substances, and distilled to remove the solvent benzene under reduced pressure to obtain 36.1 g of a transparent viscous liquid.

The viscous liquid has an active oxygen content of 3.62% measured by usual iodine titration method of Example 1.

Characteristic absorption wave lengths of the viscous liquid in IRA spectrum are 1,780 cm$^{-1}$, 1,800 cm$^{-1}$

bond of diacyl group), 1,060 cm$^{-1}$ (C—O bond) and 880 cm$^{-1}$ (—O—O—bond).

δ values and strengths of NMR spectrum of the viscous liquid are

| | | |
|---|---|---|
| ⓐ | 1.28 ppm | (12 H) |
| ⓑ | 1.45–1.60 ppm | (8 H) |
| ⓒ | 2.40 ppm | (4 H) |
| ⓓ | 2.75 ppm | (2 H) |
| ⓔ | 7.45 ppm | (10 H) |

From the above data, it is confirmed that the viscous liquid is a polymeric diacyl peroxide essentially consisting of a structural unit having the formula:

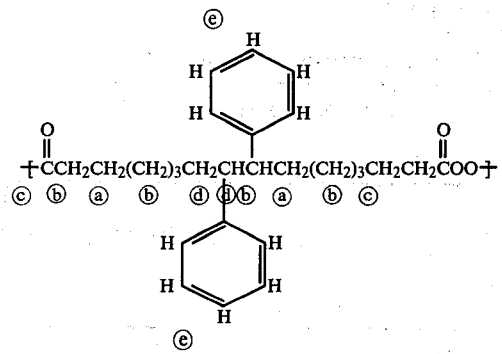

The polymeric diacyl peroxide has a mean molecular weight of 9,700 (n≅22.2) determined by a similar manner as in Example 1.

The safety degree of the polymeric diacyl peroxide and solubility thereof in various solvents are determined in the similar manner as in Example 1. The results are respectively shown in Tables 1 and 2 which will later be described.

EXAMPLE 11

The same reaction, with separation and purification as in Example 10 is repeated, except that the amount of 50% hydrogen peroxide is 5.5 g (0.8 mol) instead of 8.2 g (0.12 mol) and 47.5 g of dichloride of 7,8-diphenyltetradecane-1,14-dicarboxylic acid (purity 95%, trade name ST-2P made by Okamura Seiyu K.K.) is used, to obtain 31.1 g of a transparent viscous liquid.

The viscous liquid has an active oxygen content of 2.79% measured by usual iodine titration method of Example 1.

The viscous liquid has the same characteristic absorption waves in IRA spectrum and the same δ and strength values in NMR spectrum as those of Example 10, so that it is confirmed that it consists of the same structural unit with the polymeric diacyl peroxide of Example 10.

The polymeric diacyl peroxide has a mean molecular weight of 2,100 (n≅4.8) determined by a similar manner as in Example 1.

EXAMPLE 12

The same reaction, with separation and purification as in Example 10 is repeated, except that 134.7 g (0.24 mol) of 10% potassium hydroxide aqueous solution is used instead of 137 g (0.24 mol) of 7% sodium hydroxide aqueous solution and the amount of 50% hydrogen peroxide is 6.8 g (0.10 mol) instead of 8.2 g (0.12 mol), to obtain 38.5 g of a transparent viscous liquid.

The viscous liquid has an active oxygen content of 3.74% measured by usual iodine titration method of Example 1.

The viscous liquid has the same characteristic absorption values in IRA spectrum and the same $\delta$ and strength values in NMR spectrum as those of Example 10, so that it is confirmed that it consists of the same structural unit with the polymeric diacyl peroxide of Example 10.

The polymeric diacyl peroxide has a mean molecular weight of 16,200 ($n \approx 37.2$) determined by a similar manner as to Example 1.

COMPARATIVE EXAMPLE 1

Sodium peroxide is reacted with chloride of adipic acid to produce a publicly known solid polymeric diacyl peroxide.

From characteristic absorption wave length in IRA spectrum and $\delta$ value and strength in NMR spectrum, it is confirmed that the polymeric diacyl peroxide consists of a structural unit having the formula:

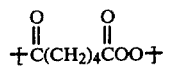

The polymeric diacyl peroxide has a mean molecular weight of 940 ($n \approx 6.5$) measured by VPO method.

The safety degree of the polymeric diacyl peroxide and solubility thereof in various solvents are determined in a similar manner as in Example 1. The results are shown in Tables 1 and 2 which will later be described.

COMPARATIVE EXAMPLE 2

Sodium peroxide is reacted with chloride of dodecanoic diacid to produce a publicly known solid polymeric diacyl peroxide.

From characteristic absorption wave length in IRA spectrum and $\delta$ value and strength in NMR spectrum, it is confirmed that the polymeric diacyl peroxide consists of a structural unit having the formula:

The polymeric diacyl peroxide has a mean molecular weight of 1,620 ($n \approx 7.1$) measured by VPO method.

The safety degree of the polymeric diacyl peroxide and solubility thereof in various solvents are shown in the following Tables 1 and 2.

TABLE 1(a)

| | | Test Results for Safety | | | | | |
|---|---|---|---|---|---|---|---|
| | Polymeric diacyl peroxide | | | | | | |
| | Structural formula | Mean molecular weight | Impact test (cm) | Friction test (kg/cm²) | (based on) TNT % | Vessel test (mm) | Explosibility |
| Example 1 | $+C(CH_2)_6CH(CH_2)_9COO+_{27.3}$ with $C_2H_5$ | 9,280 | 60 up | 700 up | 2.1 | 1.0 under | none |
| 4 | $+C(CH_2)_6CH(CH_2)_4CH(CH_2)_6COO+_{26.8}$ with $CH_3$, $CH_3$ | 9,870 | 60 up | 700 up | 1.9 | 1.0 under | none |
| 7 | $+C(CH_2)_6C=CH(CH_2)_2CH=C(CH_2)_6COO+_{20.9}$ with $CH_3$, $CH_3$ | 7,600 | 60 up | 700 up | 1.9 | 1.0 under | none |
| 10 | $+C(CH_2)_6CHCH(CH_2)_6COO+_{22.2}$ with $H_6C_5$, $C_6H_5$ | 9,700 | 60 up | 700 up | 1.3 | 1.0 under | none | of a structural unit having the formula:

TABLE 1(b)

| | | Test Results for Safety | | | | | |
|---|---|---|---|---|---|---|---|
| | Polymeric diacyl peroxide | | | | | | |
| | Structural formula | Mean molecular weight | Impact test (cm) | Friction test (kg/cm²) | (based on) TNT % | Vessel test (mm) | Explosibility |
| Comparative Example 1 | $+C(CH_2)_4COO+_{6.5}$ | 940 | 10 | 250 | 21.5 | 6.8 | occur |

TABLE 1(b)-continued

| | | Test Results for Safety | | | | | |
|---|---|---|---|---|---|---|---|
| | Polymeric diacyl peroxide | | | | | | |
| | Structural formula | Mean molecular weight | Impact test (cm) | Friction test (kg/cm$^2$) | (based on) TNT % | Vessel test (mm) | Explosibility |
| 2 | $+C(CH_2)_{10}COO+_{7.1}$ with two C=O | 1,620 | 15 | 460 | 18.9 | 4.9 | occur |

A testing method for "safety degree" was measured according to that described in Kitagawa et al., "Safety Engineering" 4(2) 131 (1965) and ibid. 7(2) 171 (1968)

TABLE 2(a)

| | | Polymeric diacyl peroxide | | Solubility (25° C., g/100 g solvent) | | | | |
|---|---|---|---|---|---|---|---|---|
| | | | Mean | Solvent | | | | |
| | | Structural formula | molecular weight | Benzene | Toluene | Styrene | Chloroform | Ethyl acetate |
| Example | 1 | $+C(CH_2)_6CH(CH_2)_9COO+_{27.3}$ with $C_2H_5$ substituent | 9,280 | 200 up | 200 up | 200 up | 200 up | 200 up |
| | 4 | $+C(CH_2)_6CH(CH_2)_4CH(CH_2)_6COO+_{26.8}$ with two $CH_3$ substituents | 9,870 | 200 up | 200 up | 200 up | 200 up | 200 up |
| | 7 | $+C(CH_2)_6C=CH(CH_2)_2CH=C(CH_2)_6COO+_{20.9}$ with two $CH_3$ substituents | 7,600 | 200 up | 200 up | 200 up | 200 up | 200 up |
| | 10 | $+C(CH_2)_6CHCH(CH_2)_6COO+_{22.2}$ with $C_6H_5$ and $C_6H_5$ substituents | 9,700 | 200 up | 200 up | 200 up | 200 up | 200 up |

TABLE 2b

| | | Polymeric diacyl peroxide | | Solubility (25° C., g/100 g solvent) | | | | |
|---|---|---|---|---|---|---|---|---|
| | | | Mean | Solvent | | | | |
| | | Structural formula | molecular weight | Benzene | Toluene | Styrene | Chloroform | Ethyl actate |
| Comparative Example | 1 | $+C(CH_2)_4COO+_{6.5}$ | 940 | 1.0 | 0.4 | 0.3 | 3.9 | 0.2 |
| | 2 | $+C(CH_2)_{10}COO+_{7.1}$ | 1,620 | 1.9 | 1.0 | 0.5 | 10.0 | 0.3 |

As apparent from the above Tables 1 and 2, the polymeric diacyl peroxide of the present invention is exceedingly safe in production and handling as compared with conventional polymeric diacyl peroxide, and dissolves quickly in solvents for vinyl monomer with exceptionably higher solubilities as compared with conventional polymeric diacyl peroxide.

EXAMPLE 13

This Example shows test results of bulk polymerization of styrene and measurement of mean molecular weight.

Samples of polymerization are prepared by dissolving 0.09 mol of the respective polymerization initiator polymeric diacyl peroxides of Table 3 in each 1 l of styrene. Five ml of the samples are sealed in glass ampules having an inner diameter of 12 mm and subjected to polymerization reaction at 70° C. for 7 hrs. Thereafter, the reaction solution are taken out, dissolved in each 50 ml of benzene. Unreacted styrene monomers are measured quantitatively by gas chromatography of internal standard method to determine polymerization conversion ratios. Subsequently, the reaction solutions in benzene are put in each 500 ml of methylalcohol to yield white precipitates of polystyrene. The white precipitates of polystyrene are dried and mean molecular weights thereof are determined by a high speed liquid chromatograph device HLC-802 UR type of Toyo Soda Kogyo K.K. The results are shown in the following Table 3.

TABLE 3

Results of Polymerization

| | | Polymerization initiator | Mean molecular weight | Polymerization conversion ratio (%) | Mean molecular weight of polystyrene ($\times 10^4$) |
|---|---|---|---|---|---|
| | | Structural formula | | | |
| Example | 1 | $+C(CH_2)_6CH(CH_2)_9COO+_{27.3}$ <br> $\quad\quad\quad\quad\|\quad\quad\quad\|$ <br> $\quad\quad\quad\quad O\quad\quad\quad C_2H_5\quad O$ | 9,280 | 97.6 | 17.5 |
| | 4 | $+C(CH_2)_6CH(CH_2)_4CH(CH_2)_6COO+_{26.8}$ <br> with $CH_3$, $CH_3$ substituents | 9,870 | 98.2 | 18.1 |
| | 7 | $+C(CH_2)_6C=CH(CH_2)_2CH=C(CH_2)_6COO+_{20.9}$ <br> with $CH_3$, $CH_3$ substituents | 7,600 | 98.4 | 18.3 |
| | 10 | $+C(CH_2)_6CHCH(CH_2)_6COO+_{22.2}$ <br> with $C_6H_5$, $C_6H_5$ substituents | 9,700 | 99.1 | 18.9 |
| Conventional prior art | | Lauroyl peroxide | *398 | 98.6 | 9.8 |

*Molecular weight

As shown in the above Table 3, the polymeric diacyl peroxide of the present invention produces polymers which have noticeably high mean molecular weight and hence high polymerization degrees as compared with those of a conventional polymerization initiator lauroyl peroxide.

EXAMPLE 14

This Example shows test results of bulk polymerization of styrene and measurement of catalyst efficiency.

Samples of polymerization are prepared by dissolving 0.02 mol of the respective polymerization initiator polymeric diacyl peroxides of Table 4 in each 1 l of styrene. Five ml of the samples are sealed in glass ampules having an inner diameter of 12 mm and subjected to polymerization at 60° C. Catalyst efficiencies of the polymerization initiators are determined respectively.

Catalyst efficiencies are measured based on the method described in "Experimental Method for Vinyl Polymerization" p. 256, published by Kyoritsu Shuppan K.K. The results are shown in the following Table 4.

TABLE 4

| | | Polymerization initiator | Mean molecular weight | Catalyst efficiency |
|---|---|---|---|---|
| | | Structural formula | | |
| Example | 1 | $+C(CH_2)_6CH(CH_2)_9COO+_{27.3}$ with $C_2H_5$ | 9,280 | 0.58 |
| | 4 | $+C(CH_2)_6CH(CH_2)_4CH(CH_2)_6COO+_{26.8}$ with $CH_3$, $CH_3$ | 9,870 | 0.62 |
| | 7 | $+C(CH_2)_6C=CH(CH_2)_2CH=C(CH_2)_6COO+_{20.9}$ with $CH_3$, $CH_3$ | 7,600 | 0.61 |
| | 10 | $+C(CH_2)_6CHCH(CH_2)_6COO+_{22.2}$ with $C_6H_5$, $C_6H_5$ | 9,700 | 0.63 |
| Comparative Example | 1 | $+C(CH_2)_4COO+_{16.5}$ | 940 | 0.26 |

TABLE 4-continued

| | Polymerization initiator | Mean molecular weight | Catalyst efficiency |
|---|---|---|---|
| | Structural formula | | |
| 2 | $+C(CH_2)_{10}COO+_{n.r.}$ with two $\overset{O}{\underset{\|}{}}$ groups | 1,620 | 0.36 |

As seen from the above Table 4, the polymeric diacyl peroxide of the present invention has exceedingly high catalyst efficiency in vinyl polymerization as compared with prior art polymerization initiator.

As described in the foregoings, the polymeric diacyl peroxide of the present invention is eminently useful industrially as a polymerization initiator for free radical polymerization of vinyl monomer.

Although the invention has been described in considerable detail with reference to certain preferred embodiments thereof, it will be understood that variations and modification can be effected within the spirit and scope of the invention as described above and as defined in the appended claims.

What is claimed is:

1. Polymeric diacyl peroxide which consists essentially of a randomly oriented repeated structural unit of a general formula $$+\overset{O}{\underset{\|}{C}}(CH_2)_5X(CH_2)_5\overset{O}{\underset{\|}{C}}OO+ \quad (1)$$

wherein X represents a group selected from the group consisting of $$-CH_2CH(CH_2)_4-,\ -CH_2CH(CH_2)_4CHCH_2-,$$
$$\ \ \ \ \ \ \ \ \ \underset{CH_2CH_3}{|}\ \ \ \ \ \ \ \ \ \ \ \ \underset{CH_3}{|}\ \ \ \ \ \ \ \underset{CH_3}{|}$$

$$-CH_2C=CH(CH_2)_2CH=CCH_2-\ \text{and}\ -CH_2CHCHCH_2-,$$
$$\ \ \ \ \ \underset{CH_3}{|}\ \ \ \ \ \ \ \ \ \ \ \ \ \ \ \ \ \underset{CH_3}{|}$$

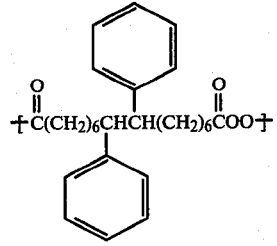

and which has a mean molecular weight of 1,400–18,000.

2. Polymeric diacyl peroxide as defined in claim 1 which consists essentially of a randomly oriented repeated structural unit of a formula:

$$+\overset{O}{\underset{\|}{C}}(CH_2)_6CH(CH_2)_9\overset{O}{\underset{\|}{C}}OO+$$
$$\ \ \ \ \ \ \ \ \ \ \ \ \ \ \ \ \underset{CH_2CH_3}{|}$$

and which has a mean molecular weight of 2,000–16,000.

3. Polymeric diacyl peroxide as defined in claim 1 which consists essentially of a randomly oriented repeated structural unit of a formula:

$$+\overset{O}{\underset{\|}{C}}(CH_2)_6CH(CH_2)_4CH(CH_2)_6\overset{O}{\underset{\|}{C}}OO+$$
$$\ \ \ \ \ \ \ \ \ \ \ \underset{CH_3}{|}\ \ \ \ \ \ \ \ \ \underset{CH_3}{|}$$

and which has a mean molecular weight of 2,000–17,000.

4. Polymeric diacyl peroxide as defined in claim 1 which consists essentially of a randomly oriented repeated structural unit of a formula:

$$+\overset{O}{\underset{\|}{C}}(CH_2)_6C=CH(CH_2)_2CH=C(CH_2)_6\overset{O}{\underset{\|}{C}}OO+$$
$$\ \ \ \ \ \ \ \ \ \ \ \ \underset{CH_3}{|}\ \ \ \ \ \ \ \ \ \ \ \ \ \ \underset{CH_3}{|}$$

and which has a mean molecular weight of 1,400–16,000.

5. Polymeric diacyl peroxide as defined in claim 1 which consists essentially of a randomly oriented repeated structural unit of a general formula:

$$+\overset{O}{\underset{\|}{C}}(CH_2)_6CHCH(CH_2)_6\overset{O}{\underset{\|}{C}}OO+$$
with phenyl substituents on the two CH carbons and which has a mean molecular weight of 1,700–18,000.

6. Polymerization initiator for vinyl monomer, comprising, as an active ingredient, the polymeric diacyl peroxide which consists essentially of a randomly oriented repeated structural unit of the general formula (1).

7. Polymerization initiator as defined in claim 6 wherein the vinyl monomer is styrene.

* * * * *